(12) United States Patent
Donders et al.

(10) Patent No.: US 8,486,915 B2
(45) Date of Patent: Jul. 16, 2013

(54) COMPOSITIONS OF WATER-INSOLUBLE ACTIVE ORGANIC COMPOUNDS

(75) Inventors: Karoly Donders, Ostermundigen (CH); Kolazi Narayanan, Wayne, NJ (US)

(73) Assignee: ISP Investments Inc., Wilmington, DE (US)

( * ) Notice: Subject to any disclaimer, the term of this patent is extended or adjusted under 35 U.S.C. 154(b) by 954 days.

(21) Appl. No.: 11/573,502

(22) PCT Filed: Aug. 11, 2005

(86) PCT No.: PCT/US2005/028681
§ 371 (c)(1),
(2), (4) Date: Jul. 27, 2009

(87) PCT Pub. No.: WO2006/028649
PCT Pub. Date: Mar. 16, 2006

(65) Prior Publication Data
US 2009/0293762 A1     Dec. 3, 2009

(30) Foreign Application Priority Data
Aug. 12, 2004   (CH) ..................................... 1335/04

(51) Int. Cl.
*A01N 43/64*   (2006.01)
*A01N 43/653*   (2006.01)

(52) U.S. Cl.
USPC ........ 514/68; 514/383; 252/380; 252/182.11; 252/182.26; 106/18; 106/18.29; 106/18.32

(58) Field of Classification Search
USPC . 106/18, 18.29, 18.32; 514/383, 68; 252/380, 252/182.11, 186.26
See application file for complete search history.

(56) References Cited

U.S. PATENT DOCUMENTS

| | | | |
|---|---|---|---|
| 5,212,213 A * | 5/1993 | Hutter .............................. | 522/81 |
| 5,228,905 A * | 7/1993 | Grunewalder et al. ........... | 106/2 |
| 5,596,032 A * | 1/1997 | Schilling et al. ................ | 524/60 |
| 6,217,889 B1 * | 4/2001 | Lorenzi et al. ................. | 424/401 |
| 6,242,398 B1 * | 6/2001 | Chambers et al. ............. | 510/151 |
| 2005/0031547 A1 * | 2/2005 | Tamarkin et al. ............... | 424/45 |
| 2007/0020304 A1 * | 1/2007 | Tamarkin et al. ............. | 424/405 |
| 2008/0081059 A1 * | 4/2008 | Narayanan et al. ........... | 424/405 |

* cited by examiner

*Primary Examiner* — Joseph D Anthony
(74) *Attorney, Agent, or Firm* — William J. Davis; Thompson Hine LLP

(57) ABSTRACT

A concentrate suitable for forming a stable aqueous composition upon dilution with water includes a water-insoluble active organic compound and a water-insoluble oil-modified alpha-beta unsaturated carboxylic acid.

19 Claims, No Drawings

COMPOSITIONS OF WATER-INSOLUBLE ACTIVE ORGANIC COMPOUNDS

BACKGROUND OF THE INVENTION

1. Field of the Invention

This invention relates to concentrates and aqueous use compositions of water-insoluble active organic compounds which do not require the use of emulsifiers and/or surfactants to provide stable compositions.

2. Description of the Prior Art

Aqueous compositions of a water-insoluble active organic compound such as biocides, fungicides, bactericides, insecticides, herbicides, algicides, light stabilizers, disinfectants, UV absorbers, synthetic hydrocarbons, radical scavengers, resins and natural waxes, usually require an emulsifier or surfactant solvent to formulate a stable system suitable for delivery of the active onto coatings, wood and plant surfaces, to protect them against microbiological attack. However, such formulations are quite susceptible to wash-out during heavy rain which reduces the effectiveness of such protection.

Accordingly, it is an object of this invention to provide a concentrate of a water-insoluble active organic compound which is suitable for forming a stable aqueous composition upon addition of water, without the use of emulsifiers or surfactants, and whereby the composition can deliver the water-insoluble active organic compound as an extremely fine droplets and/or particles, to a desired site.

Another object herein is to provide a stable aqueous use composition of a water-insoluble active organic compound and a water-insoluble oil-modified partially esterified dicarboxylic acid anhydride, whereby the active can be delivered effectively onto various surfaces including coatings, wood or plant surfaces, and which are water-resistant, to deliver microbiological protection for the substrate material.

A specific object of the invention is to provide such concentrate and aqueous use composition of the water-insoluble active organic compound 3-iodo-2-propyl butyl carbamate (IPBC), which, in crystalline form, is particularly effective against blue and mold fungi, while, at the same time does not exhibit the strong yellowing effect when subjected to UV radiation or lose its biocidal effectiveness upon UV decomposition.

Still another object herein is to provide such a concentrate and aqueous use compositions which can be easily applied to a target surface and form a film thereon which would protect the active during the drying process and from wash-off during rainfall.

These and other objects and features of the invention will be made apparent from the following description.

SUMMARY OF THE INVENTION

A concentrate suitable for forming a stable aqueous use composition upon dilution with water, comprising:
(a) a water-insoluble active organic compound, and
(b) a water-insoluble oil-modified alpha-beta unsaturated carboxylic acid.

Suitably, (a) is a biocide, fungicide, bactericide, insecticide, herbicide, algicide, light stabilizer, disinfectant, UV absorber, synthetic hydrocarbon, radical scavenger, resin or a natural wax, preferably IPBC and/or propiconcozole.

Preferably (b) is a partially esterified dicarboxylic acid, e.g. the half-ester of maleic acid.

Suitably, the oil is linseed oil, a glyceryl ester, mono-, di- or tri-esters, e.g. glyceryl linoleate, phytyl linoleae, castor oil, rapeseed oil, tall oil, sunflower oil, soya bean oil, palm oil, coco oil and/or safflower oil; preferably, (b) is the linseed oil-modified half-ester of maleic acid.

Suitably, (a) is present in the concentrate, in a weight %, of 5-40%; preferably 10-30%; and (b) is 40-80%, preferably 50-70%.

Preferably, the concentrate includes a cosolvent, e.g. polyethylene glycol.

Preferably, the concentrate also includes a neutralizer so that the pH is <7.

DETAILED DESCRIPTION OF THE INVENTION

The active organic compound in the concentrate and aqueous use composition of the invention is a water-insoluble organic compound such as a biocide, fungicide, bactericide, insecticide, herbicide, algicide, disinfectant, light stabilizer, UV absorber, hydrocarbon, radical scavenger, synthetic resin and/or natural wax compound. Representative anti-bacterials include IPBC and permethrin.

The active suitably is present in the concentrate in an amount by weight, of about 5-40% of the concentrate, preferably about 10-30%, and most preferably about 15-20%.

The oil component of the concentrate is a vegetable oil which is derivatized or modified to provide an ionizable functionality which provides high solubility for the active material while upon dilution with water provides a sufficient hydrophobic environment to include the active in water with the ionic or polar functionality pointing into the water phase.

Such a modified oil is a hydrophobic oil or ester such as a glyceride oil containing at least two double bonds capable of reacting with an alpha, beta-unsaturated carbonyl compound with at least one carboxylate or ionizable moiety to form a stable adduct. Suitable oil-modifiers include linseed oil, glyceryl esters, mono, di and preferably tri-esters, e.g. glyceryl linoleate, phytyl linoleae, castor oil, rapeseed oil, tall oil, sunflower oil, soya bean oil, palm oil, coco oil and/or safflower oil. A preferred oil is linseed oil.

The alpha-beta unsaturated compound to be oil-modified suitably is, partially esterified maleic acid anhydride, cinnamic acid, adipic acid, crotonic acid, gluratic acid or itaconic acid. A preferred compound is the half-ester of a dicarboxylic acid such as maleic acid.

The linseed oil-modified dicarboxylic acid half-ester of maleic acid is commercially available as Bomol® 4 (Ashland Chemical). Other suitable adducts include maleated castor oil (Ceraphyl® maleated TS 874); or maleated rapeseed oil (John L. Seaton & Co. Ltd, RMT).

The oil-modified unsaturated carboxylic acid suitably is present in the concentrate in an amount by weight, of about 40-80%, preferably about 50-70%.

Storage stability of an invention concentrate which contains a water-sensitive active, e.g. a hydrolytically labile anti-bacterial such as IPBC or permethrin, can be enhanced by treating the concentrate with a dehydrating agent or water-scavenger, e.g. $P_2O_5$, CaO, anhydrous salt, epoxidized vegetable oil or carbodiimide.

With acid-sensitive actives such as IPBC it is desirable to include a neutralizing agent in the compositions, e.g. an inorganic or organic base, e.g. NaOH, $NH_3$, aminomethylpropanol (AMP), triethanolamine, a bulky or hindered amine, to provide a pH >7, e.g. 7.5. The amount of neutralizer added is generally between 3-15% of the concentrate.

If desired, a cosolvent may be included in the concentrate, e.g. cyclic amide such as N-methylpyrrolidone, N-octyl pyrrolidone and N,N-dimethyl imidazolidone; and alkyl esters ($C_1$-$C_4$) of carboxylic acids ($C_6$-C-is); or C2-C4 alkyl ethers of polyalkylene glycols; amides such as dimethyl formamide, lactones, such as butyrolactone; aliphatic, aromatic and alicyclic hydrocarbons, such as Exxon aromatic 100, 150 or 200; heptane dodecene and/or cyclohexanone.

Optional co-formulating agents include polymeric dispersants, polyethylene glycol (PEG 500), polyacrylates, Easy-Sperse® (ISP), Easy-Sperse/PVP (ISP), PVP and VP copolymers, and microemulsion-forming matrixes, e.g. Microflex NX® (ISP), in an amount of about 1-40%, preferably about 3-20%, and most preferably 10%, of the oil-derivative.

EXAMPLES

Example A 500 g of maleic acid anhydride was partially esterified with ethyl alcohol. The partial ester was mixed with 900 g of linseed oil and pressure-cooked for 3-4 hours at 160° C. with stirring. The remaining acid groups were neutralized with aminomethylpropanol to a pH of 7.

Example A-1

100 g of IPBC was dissolved in 900 g of the modified linseed oil of Example A. This solution, referred to herein as a concentrate, was ready for use as a fungicide.

Color Sample 1

2 g of the concentrate of Example A-1 was added to 100 g of white dispersion paint for exterior use.

Color Sample 2

Comparative Example 2 g of a 10% IPBC solution in butyl glycol was added to 100 g of white dispersion paint for exterior use.

Both color samples 1 and 2 were applied to separate pieces of wood and weathered at a 45° angle.
Weather Test Color Sample 1: After 3 months there was no discernible yellowing and no growth of fungus.

Color Sample 2: After 3 months severe yellowing was discernible with slight growth of fungus.
Leaching Test Fungus growth test on agar: (*aspergillus niger, Penicillium funiculosum, alternaria alternata*), painted on veneer wood.

|  | 4 weeks in water, leached out | not leached out |
| --- | --- | --- |
| Color sample 1: | No growth of fungus on the wood, growth of fungus to the edge of the wood (no zone of inhibition) | no growth of fungus on the wood growth of fungus to the edge of the wood (no zone of inhibition) |
| Color sample 2: | Slight growth of fungus on the wood, small zone without growth around the wood growth (no zone of inhibition) | no growth of fungus on the wood, small zone without around the wood (no zone of inhibition) |

Example B 20 g of propiconazole was dissolved in 80 g of the oil-modified adduct compound of Example A. The concentrate then was mixed with 10 liters of water and stirred. A very fine distribution in the water resulted; it possessed high stability. The active concentration was 0.2%, which is suitable for spray applications onto agricultural products.

Example C 20 g of alkyd resin was dissolved in 80 g of the adduct of Example A, and mixed with 1 liter of water. A stable and very fine distribution of the alkyd resin resulted, which was used as a binding agent in impregnations.

Example D 10 g of beeswax was dissolved in 90 g of the adduct compound of Example A, and mixed with 1 liter of water. A stable and very fine distribution of the wax was obtained which was used as a treatment agent for wood surfaces.

Example E 25 g of permethrin was dissolved in 75 g of the oil addition compound of Example A. A clear concentrate was obtained. Dilution of the concentrate with water at ratios of 1/10, 1/100 and 1/1000 produced optically clear aqueous use compositions without separation for 2 weeks.

Example F

Example E was modified by buffering the composition to pH 4.0 (at 1/10 dilution) by introducing a hydrophobic acid Rhodofac® RM 710, Easy-Sperse®, ordodecyl benzene sulfonic acid. Added stability against hydrolysis was obtained.

Example G

Modified linseed oil was prepared as shown in Example A, except the modified oil was neutralized with AMP to pH 4. This concentrate was used to formulate a permethrin active. 20 g Permethrin and 80 g of the modified oil was neutralized to pH 4.0 (1/10 dilution). A stable clear solution was obtained. On dilution at 1/10, 1/100 and 1/1000 ratios, stable use compositions were obtained.

Example H 20 g IPBC was dissolved in 80 g Ceraphyl RMT (commercially available maleated castor oil) neutralized with AMP to pH near 7.0 (at 1/10 dilution). Very good efficacy was observed when compared to the untreated sample.

Example 1

10% of iodine carbamate (IPBC) was dissolved in a chemically maleated modified linseed oil (John I. Seaton & Co. Ltd., YS 873), resulting in a clear, almost colorless solution (Gardner ASTM D 1544-80=6) with a pH value between 4 and 6.

This concentrate dispersed well in water, forming an emulsion with particle sizes between 20 and 60 micrometers in the oily phase. Emulsions with 1 to 4% oil phase in water were stable for at least 6 days without the IPBC turning out in crystalline form.

A check at the weathering stand brought abut the following results: IPBC was brought into a white pigmented acrylate dispersion; the coating was applied on wood and exposed to weather conditions.

TABLE 1

| Product | IPBC Conc. | Yellowing 6 months | Yellowing 1 year | Fungi Fouling 6 months | Fungi Fouling 1 year |
|---|---|---|---|---|---|
| Seaton YS 873 | 0.1% | none | none | slight | slight |
| Seaton YS 873 | 0.5% | none | none | none | none |
| Butylglycol | 0.1% | slight | distinct | slight | strong |
| Butylglycol | 0.5% | strong | strong | distinct | strong |
| Fungitrol B10 | 0.1% | none | none | none | none |

Example 2

As described in Example 1, 10% of iodine carbamate was dissolved in a chemically modified oil, rapeseed oil (John L. Seaton & Co. Ltd., YS 874), resulting in a clear, almost colorless solution (Gardner ASTM D 1544-80=6) with a pH value between 4 and 6.

This concentrate dispersed well in water, forming an emulsion with particle sizes between 20 and 60 micrometers in the oily phase. Emulsions with 1 to 4% oil phase were stable for at least 6 days without the IPBC turning out in crystalline form.

A check at the weathering stand brought abut the following results: IPBC was brought into a white pigmented acrylate dispersion; the coating was applied on wood and exposed to weather conditions.

TABLE 2

| Product | IPBC Conc. | Yellowing 6 months | Yellowing 1 year | Fungi Fouling 6 months | Fungi Fouling 1 year |
|---|---|---|---|---|---|
| Seaton YS 874 | 0.1% | none | none | slight | slight |
| Seaton YS 874 | 0.5% | none | none | none | none |
| Butylglycol | 0.1% | slight | distinct | slight | strong |
| Butylglycol | 0.5% | strong | strong | distinct | strong |
| Fungitrol B10 | 0.1% | none | none | none | none |

Example 3

10% of iodine carbamate each was dissolved in differently modified, oxidatively drying oils (Resydrol® VAL 5547w and Resydrol® VAL 7149w) as well as in oxidatively drying alkyd resin, which became soluble in water after neutralization. When stirred up into water, the formulations formed emulsions.

The other tests were carried out as described in Examples 1 and 2.

TABLE 3

| Product | IPBC Conc. | Yellowing 6 months | Yellowing 1 year | Fungi Fouling 6 months | Fungi Fouling 1 year |
|---|---|---|---|---|---|
| Resydrol VAL5547w | 0.1% | none | none | slight | slight |
| Resydrol VAL5547w | 0.5% | none | none | none | none |
| Resydrol VAL5547w | 1.0% | none | slight | none | none |
| Resydrol VAL5547w + 10% HALS | 1.0% | none | none | none | none |
| Resydrol VAL7149w | 0.1% | none | none | slight | slight |
| Resydrol VAL7149w | 0.5% | none | none | none | none |
| Resydrol VAL5527w | 0.1% | none | none | slight | distinct |
| Resydrol VAL5527w | 0.5% | none | none | none | none |
| Butylglycol | 0.1% | slight | distinct | slight | strong |
| Butylglycol | 0.5% | strong | strong | distinct | strong |
| Fungitrol B10 | 0.1% | none | none | none | none |

Preferred formulations of the invention are given below:

| Ingredient | Amount (wt %) |
|---|---|
| Funcitrol ® B10 | |
| IPBC | 10.0 |
| Kathon ® 893F | 5.5 (45% in glycol) |
| Bomol ® 4 | 69.8 |
| AMP 100 | 4.7 |
| PEG 400 | 10.0 |
| | 100.0 |
| Funqitrol ® B30 | |
| IPBC | 10.0 |
| Propiconazol | 20.0 |
| Kathon ® 893F | 5.5 |
| Bomol ® 4 | 51.1 |
| AMP 100 | 3.4 |
| PEG 400 | 10.0 |
| | 100.0 |

While the invention has been described with particular reference to certain embodiments thereof, it will be understood that changes and modifications may be made which are within the skill of the art.

What is claimed is:

1. A concentrate suitable for forming a stable aqueous composition upon dilution with water, comprising:
    (a) a water-insoluble active organic compound selected from the group consisting of a biocide, a fungicide, a bactericide, an insecticide, a herbicide, an algicide, a light stabilizer, a disinfectant, a UV absorber, a synthetic hydrocarbon, a radical scavenger, a resin and a natural wax and
    (b) a water-insoluble linseed oil-modified half-ester of maleic acid and,
    wherein the concentrate is free from emulsifiers.

2. A concentrate according to claim 1 wherein component (a) is 5-40% by weight of the concentrate; and component (b) is 40-80% by weight of the concentrate.

3. A concentrate according to claim 1 wherein component (a) is 10-30% by weight of the concentrate; and component (b) is 50-70% by weight of the concentrate.

4. A concentrate according to claim 1 wherein component (a) is 3-iodo-2-propyl butyl carbamate.

5. A concentrate according to claim 1 further comprising a cosolvent.

6. A concentrate according to claim 5 wherein said cosolvent is polyethylene glycol.

7. A concentrate according to claim 1 further comprising a neutralizer.

8. A concentrate according to claim 1 wherein component (a) is 3-iodo-2-propyl butyl carbamate and the pH of the concentrate is <7.

9. The concentrate according to claim 1 wherein component (a) further comprises propiconazole.

10. The concentrate according to claim 4 wherein component (a) further comprises propiconazole.

11. A method of preparing the concentrate according to claim 1 comprising
   (a) mixing maleic anhydride with an alcohol;
   (b) treating the product of step (a) with linseed oil;
   (c) neutralizing the product of step (b); and
   (d) adding a water-insoluble active organic compound selected from the group consisting of a biocide, a fungicide, a bactericide, an insecticide, a herbicide, an algicide, a light stabilizer, a disinfectant, a UV absorber, a synthetic hydrocarbon, a radical scavenger, a resin and a natural wax.

12. The method according to claim 11 wherein the water-insoluble active organic compound is 3-iodo-2-propyl butyl carbamate.

13. The method according to claim 11 wherein the water-insoluble active organic compound is propiconazole.

14. A method of controlling fungus at a locus comprising applying to a locus an effective amount of the concentrate according to claim 4 wherein the concentrate is diluted into water before application to the locus.

15. The method according to claim 14 wherein the locus is an agricultural locus.

16. The method according to claim 14 wherein the locus is a non-agricultural locus.

17. A method of controlling fungus at a locus comprising applying to a locus an effective amount of the concentrate according to claim 9 wherein the concentrate is diluted into water before application to the locus.

18. The method according to claim 17 wherein the locus is an agricultural locus.

19. The method according to claim 17 wherein the locus is a non-agricultural locus.

* * * * *